Figure 1:
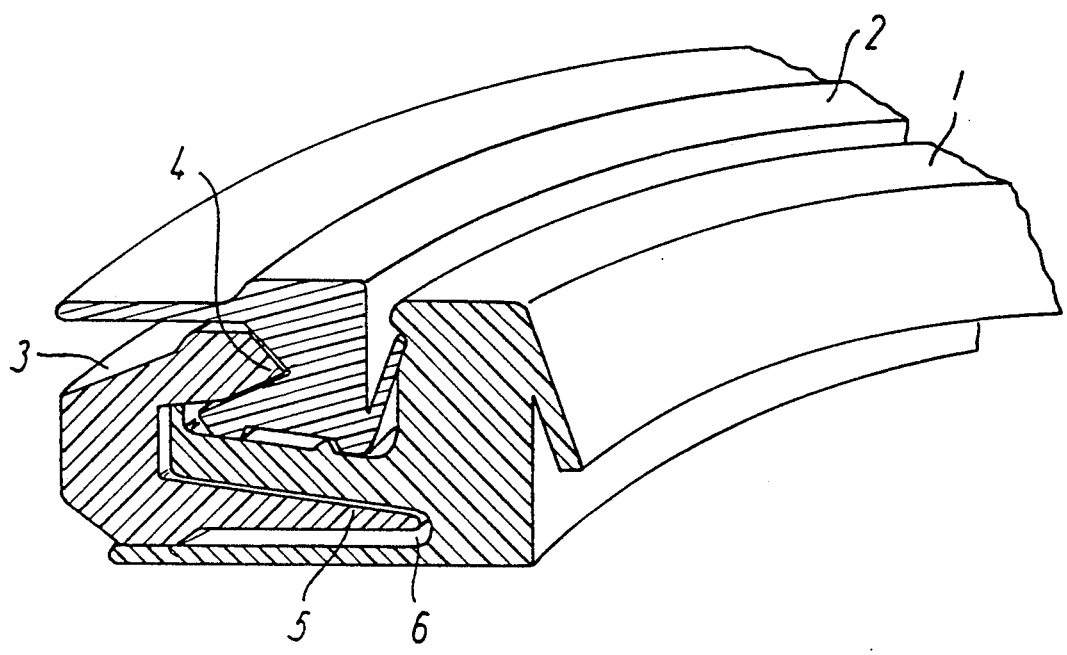

United States Patent [19]

Olsen

[11] Patent Number: 5,322,522
[45] Date of Patent: Jun. 21, 1994

[54] LOCKING RING FOR AN OSTOMY COUPLING

[75] Inventor: Hans Olsen, Bronshoj, Denmark

[73] Assignee: Coloplast A/S, Denmark

[21] Appl. No.: 809,528

[22] PCT Filed: Jul. 20, 1990

[86] PCT No.: PCT/DK90/00193

§ 371 Date: Mar. 19, 1992

§ 102(e) Date: Mar. 19, 1992

[87] PCT Pub. No.: WO91/01119

PCT Pub. Date: Feb. 7, 1991

[30] Foreign Application Priority Data

Jul. 21, 1989 [DK] Denmark ................ 3618/89

[51] Int. Cl.⁵ .................................................. A61F 5/44
[52] U.S. Cl. ........................................ 604/342; 604/332; 604/338; 604/339
[58] Field of Search ......... 604/332, 338, 339, 340–344

[56] References Cited

U.S. PATENT DOCUMENTS

| 3,869,762 | 3/1975 | Barrett et al. | 604/342 |
| 4,623,338 | 11/1986 | Larson . | |
| 4,973,324 | 11/1990 | Steer | 604/342 |
| 5,026,360 | 6/1991 | Johnson et al. | 604/338 |
| 5,180,377 | 1/1993 | Holtermann | 604/342 |

FOREIGN PATENT DOCUMENTS

| 134263 | 10/1976 | Denmark . |
| 255310 | 2/1988 | European Pat. Off. . |
| 1105558 | 4/1961 | Fed. Rep. of Germany . |
| 119437 | 5/1970 | Norway . |
| 2201345 | 9/1988 | United Kingdom . |
| 2215212 | 9/1989 | United Kingdom . |

Primary Examiner—Randall L. Green
Assistant Examiner—Rob Clarke
Attorney, Agent, or Firm—Ostrolenk, Faber, Gerb & Soffen

[57] ABSTRACT

For an ostomy coupling comprising a patient part and a bag part a locking ring for mutually retaining these parts is disclosed. The locking ring has a first locking mechanism with two positions of the locking ring, in which the coupled parts are mutually loosely connected and mutually locked, respectively. The locking ring furthermore has a second locking mechanism being independent of the first locking mechanism and adapted for retaining and releasing, respectively, the locking ring relatively to one of the parts.

7 Claims, 5 Drawing Sheets

LOCKING RING FOR AN OSTOMY COUPLING

The present invention relates to a locking ring for an ostomy coupling comprising a first part with a neck, a second part with a collar adapted to be coupled in tight-fitting relationship with the neck of the first part, one of said parts being intended to be attached to a patient, the other part being secured to a collection bag, the locking ring being adapted for mutually retaining said parts.

The invention is primarily constructed for use in connection with a lockable coupling for retaining ostomy equipment, such as bags for collection of evacuations from surgically formed, artificial intestinal orifices, and for retaining closure-like locking devices for such artificial body orifices.

Such couplings are usually annular and the part intended to be attached to a patient (in the following called the patient part) is often provided with a plate or flange applied with an adhesive by which the patient part is adhered to the patient's skin and which is generally changed at an interval of several days. The second part of the coupling, which is secured to a bag for collecting faeces, in the following called the bag part, must for obvious reasons be completely tight-fitting to the patient part.

EP 255 310 discloses an ostomy coupling with a locking ring providing a locking mechanism for the coupled parts but with no releasable locking mechanism for its retention to one of the parts to be coupled.

Manipulation of the coupling parts during assembling and disassembling may cause great pain especially to newly operated ostomy patients, and consequently it is important that such manipulation transfers as few and small force loads as at all possible to the patient. This need makes heavy demands on both the coupling parts and their locking mechanism.

Consequently, it is desirable to provide a locking mechanism for a coupling of the kind described allowing assembling and disassembling to be performed without causing heavy force loads, and in which the coupling parts are retained together by a locking mechanism which can be brought into and out of engagement in a simple way without causing any appreciable force load. It is furthermore important that the coupling besides the patient part and the bag part comprises no other loose or separate parts, so that assembling and disassembling can be performed quickly, in a simple and safe way.

It is the object of the present invention to provide a locking ring for an ostomy coupling, which meets these requirements.

According to the invention this object is achieved by a construction as stated in the characterizing portion of claim 1.

By the locking ring having two different locking mechanisms it is achieved that the patient when changing bag, which involves disassembling and assembling of the patient part and bag part of the coupling, operates the first locking mechanism, which in one position allows bag changing, and in the other position retains the bag part relatively to the patient part. As the two locking mechanisms are mutually independent, the second locking mechanism is not influenced when activating the first locking mechanism. To the patient this means that when changing bag the locking ring is always connected to one of the coupling parts so that there is no risk of it falling off. During assembling there is thus only two parts, viz. bag part and patient part, to be placed in correct mutual relationship.

In claims 2 and 3 are stated advantageous, different release operations for the two locking mechanisms.

In claim 4 is stated that the locking ring has radially resilient tongues. When changing bag these tongues ensure the centering of the locking ring relatively to the part to which it is secured, thus facilitating the positioning of the bag part.

Figure 2:
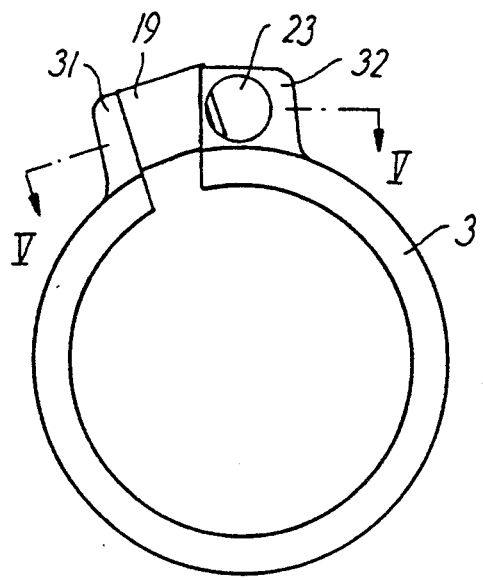
Figure 3:
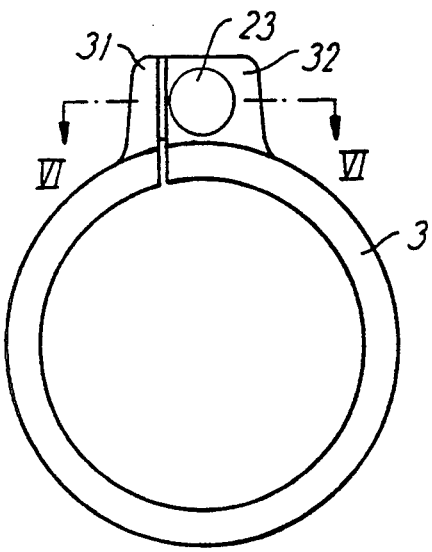
Figure 4:
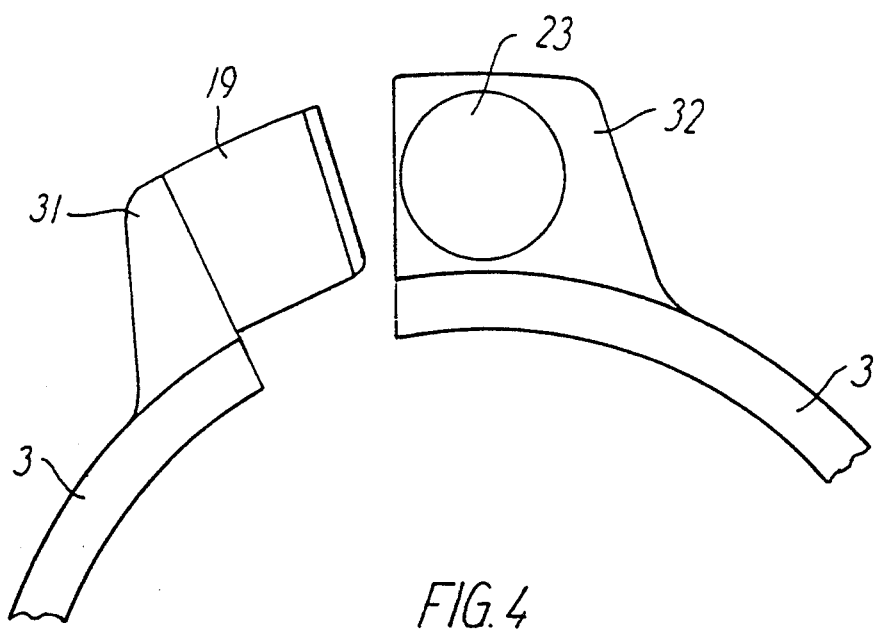
Figure 5:
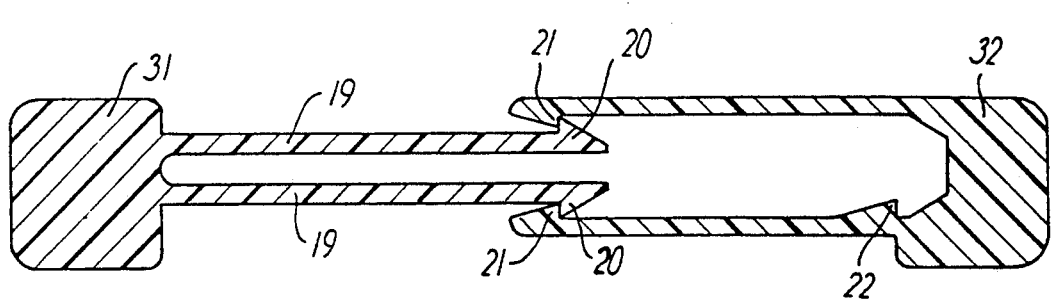
Figure 6:
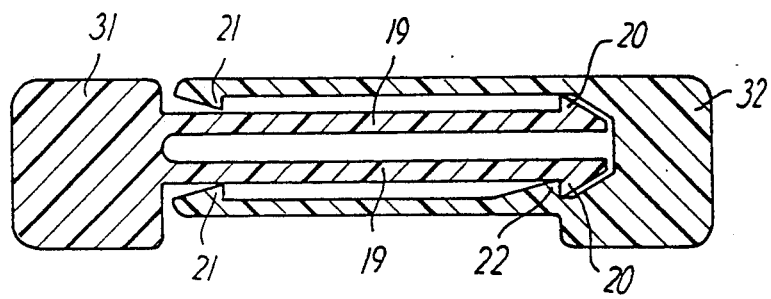
Figure 7:
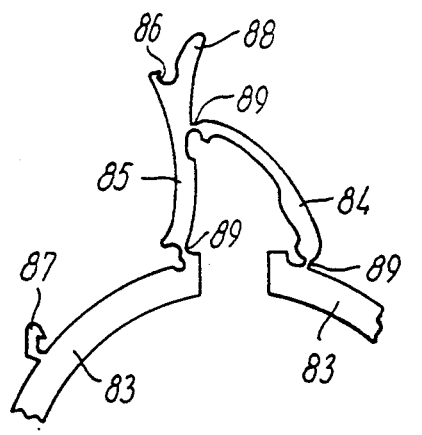
Figure 8:
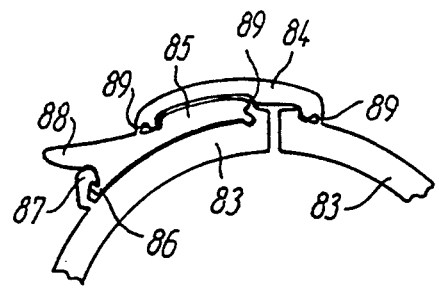
Figure 9:
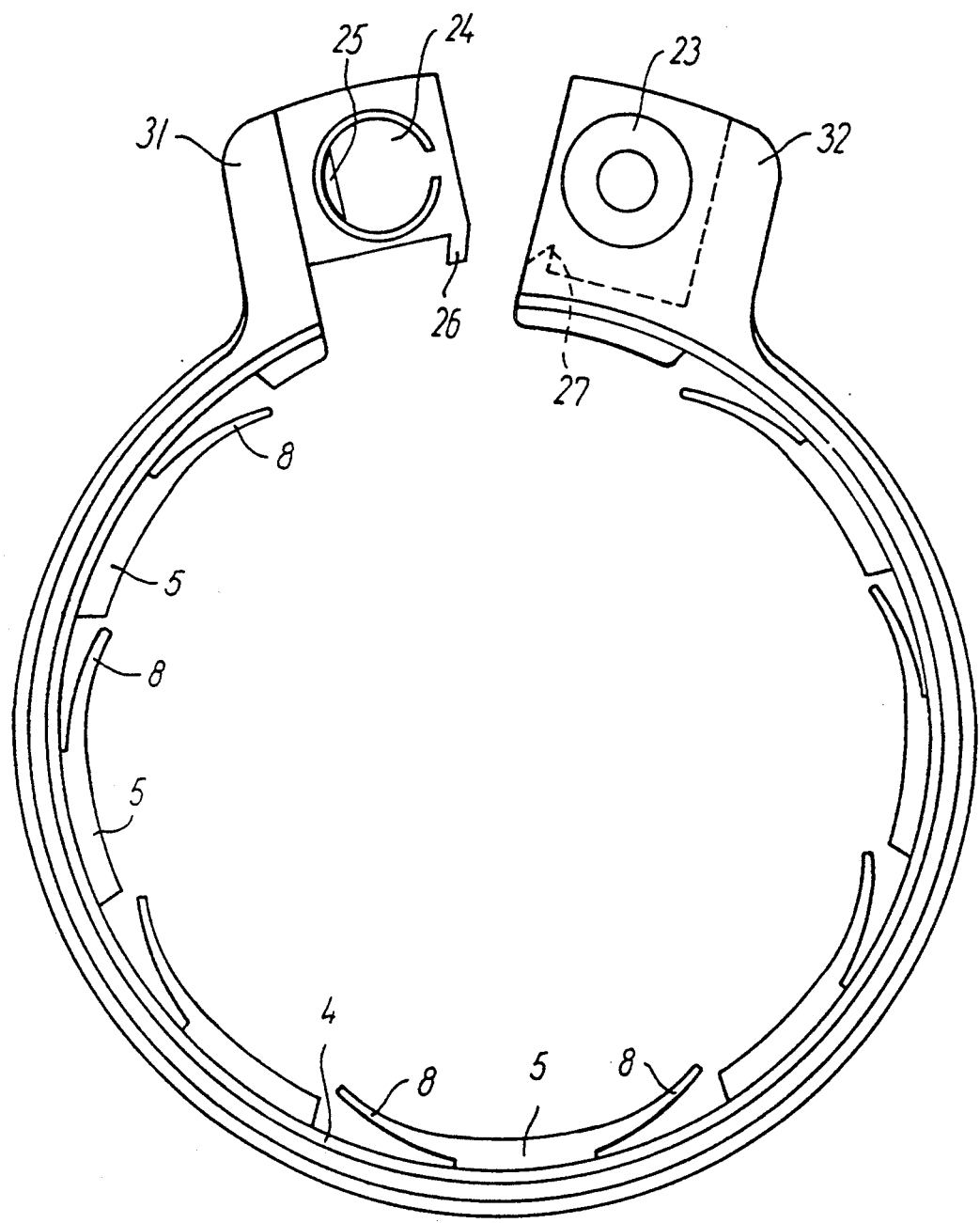
Figure 10:
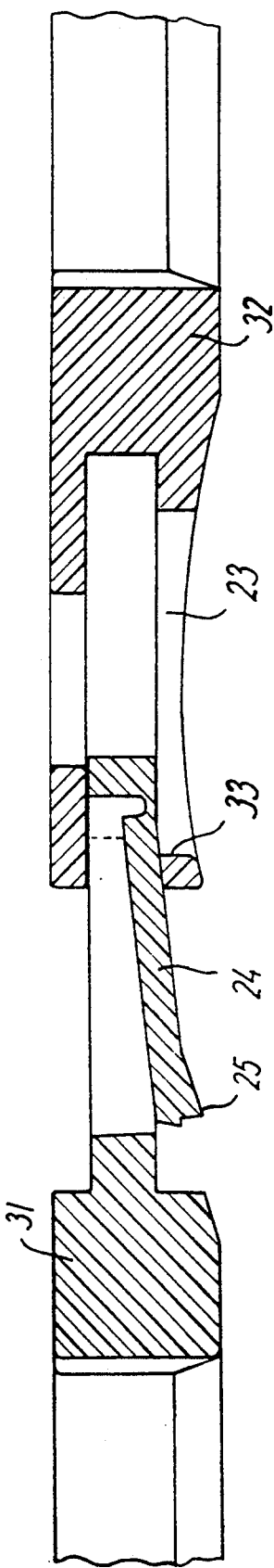
Figure 11:
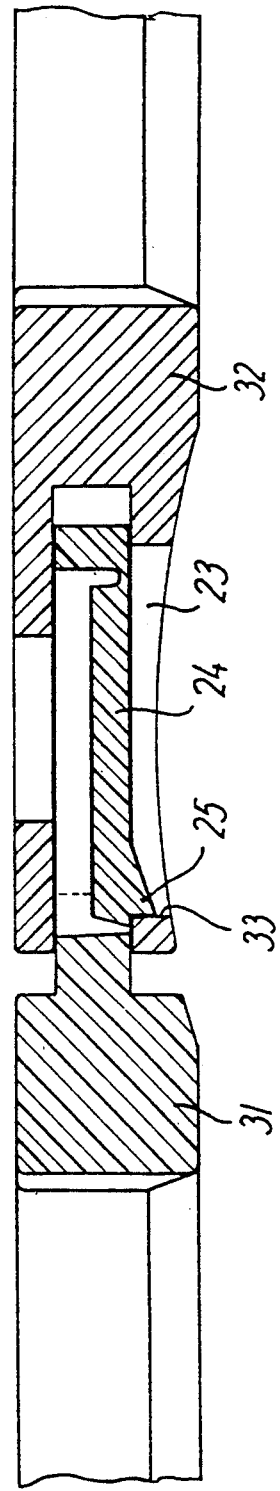

In the following the invention is described in more detail, reference being made to the drawing in which FIG. 1 shows a perspective view of a radial section of a part of a locking ring according to a preferred embodiment of the invention together with an ostomy coupling, FIG. 2 shows the locking ring in a pre-locked position, FIG. 3 shows the locking ring in FIG. 2, but in a locked position, FIG. 4 shows a part of the locking ring in a completely unlocked position, FIG. 5 shows a section through the locking mechanism of the locking ring in the pre-locked position, FIG. 6 shows a section through the locking mechanism of the locking ring in the locked position, FIGS. 7 and 8 show parts of an alternative embodiment of the locking ring in pre-locked and locked position, respectively, FIG. 9 shows a preferred embodiment of the locking ring according to the invention in completely unlocked position, and FIG. 10 and 11 show a section through the locking mechanism of the locking ring in FIG. 9 in pre-locked and locked position, respectively.

FIG. 1 shows an annular patient part 1 which at its under side is adapted for being secured onto a not shown adhesive plate or flange by which the patient part 1 is positioned on the patient's skin around an ostomy orifice. An annular bag part 2 is at its upper side adapted for being connected to a not shown bag for collecting faeces from the ostomy orifice. A locking ring 3 is here shown in a locked position in which it retains the bag part 2 in position relative to the patient part 1.

The locking ring 3 has an inwardly projecting part 4 being shaped as an outwardly open V, and which when tightening and locking the locking ring engages with a corresponding recess in the bag part 2. The locking ring 3 has a second inwardly projecting part 5 positioned in a recess 6 in the patient part 1 of the ostomy coupling. In FIG. 1 the locking ring 3 is shown in its locked position, in which with its inwardly projecting parts 4 and 5 it retains the bag part 2 in position relative to the patient part 1.

The locking effect, i.e. the tightening of the bag part 2 and the patient part 1 is derived from the locking ring 3. FIGS. 2–4 show the locking ring 3, which is interrupted by an almost radial cut so as to be capable of assuming the three positions shown in FIGS. 2–4, respectively. FIG. 2 shows the locking ring in a pre-locked position, which is the position it is in when the coupling is supplied to the user and when being attached to the user's body, and which permits changing of the ostomy bag, as the coupled parts here are mutually loosely connected. FIG. 3 shows the locking ring 3 in a locked position in which it is also shown in FIG. 1, and in which the bag part 2 is retained in position relative to the patient part 1. FIG. 4 shows on an enlarged scale parts of the locking ring in completely open position, which position the locking ring has during manufacture by moulding, and in which it can be positioned on the patient part 1. The locking ring 3 is preferably moulded in an elastic resilient material, and will thus naturally seek to assume the completely unlocked position shown in FIG. 4. When locking mechanisms for the locked and pre-locked position, respectively, of the ring are released, the locking ring will consequently due to its resiliency by it self spring open and assume the pre-locked or the completely unlocked position, respectively.

It should be noted that in each of the three positions of the locking ring, the pre-locked, the locked and the completely unlocked position, respectively, it has three different diameters.

As is seen from FIG. 1 the inwardly projecting part or edge 5 of the locking ring has an internal diameter which is smaller than that of the part 4 of the locking ring. These internal diameters are so adapted that in the pre-locked position of the ring in FIG. 2, the diameter of the part 4 of the locking ring, which part retains the bag part, is increased precisely so much compared to the locked position in FIGS. 1 and 3 that the bag part 2 and the patient part 1 can easily be assembled and disassembled by a mutual axial movement. In this pre-locked position of the locking ring, the part 5 of the locking ring is still in engagement with the corresponding annular recess 6 in the patient part 1, and the locking ring is thus in its pre-locked position retained on the patient part.

Not until the locking ring 3 is opened to assume its completely unlocked position in FIG. 4 can also the locking ring be released from the patient part 1.

FIG. 5 shows a section through the pre-locked locking mechanism of the locking ring along the line V—V in FIG. 2, and FIG. 6 shows a section through the locked locking mechanism of the locking ring along the line VI—VI in FIG. 3. On a radially outwardly projecting protrusion 31, the locking ring is provided with two elastic, axially resilient flaps 19 which at their tips have axially outwardly projecting hooks 20, which in the pre-locked position in FIG. 5 abut against corresponding inwardly directed hooks 21, and in the locked position in FIG. 6 abut against a hook 22. The hooks 21 and 22 are provided on a radially outwardly projecting protrusion 32. In order to activate this locking mechanism so as to pass from the pre-locked position in FIGS. 2 and 5 to the locked position in FIGS. 3 and 6 the two protrusions 31 and 32 of the locking ring are pressed together, and one of the hooks 20 enters into a clicking-engagement with the hook 22. Through an opening 23 it possible by a slight touch of a finger to bring the hooks 20 and 22 out of engagement, whereby the locking mechanism reassumes the pre-locked position in FIGS. 2 and 5.

In order to release the locking mechanism completely, the hooks 20 must be released from the hooks 21, and with a suitable construction of the hooks this is done in that the protrusion 31 with the flaps 19 by a radial movement are lifted free of the hooks 21 so that the locking ring assumes the unlocked position shown in FIG. 4.

FIG. 9 shows the preferred embodiment of the locking ring according to the invention in its completely unlocked state. Similarly to FIGS. 5 and 6 FIGS. 10 and 11 show a section through the locking mechanism in FIG. 9 of the locking ring in pre-locked and locked position, respectively. A flap 24 here corresponds to the flaps 19 in FIGS. 5 and 6, and the flap 24 has an axially outwardly projecting hook 25 corresponding to the hooks 20 in FIGS. 5 and 6, which in the locked position of the ring in FIG. 11 is in a clicking-engagement with a corresponding hook 33 on the part 32. Further, the locking ring in FIG. 9 has on respective ones of the protrusions 31 and 32 two hooks 26 and 27. In the pre-locked position of the locking ring these hooks are in mutual engagement, and the locking ring may be made to assume its completely unlocked position in that the hook 26 by a radial movement is released from the hook 27. From the completely unlocked position the locking ring is easily made to assume both the pre-locked and the locked position by tightening the locking ring.

In FIG. 9 it is further seen that some of the parts 5 of the locking ring are provided with radially inwardly projecting resilient tongues 8, the tips of which lie on a circle having a diameter which is smaller than that of the parts 5. These resilient tongues 8 will also in the pre-locked position of the locking ring be in radial contact with the bottom of the annular groove 6 in the patient part 1, and thus also in the pre-locked position of the locking ring ensure centering of the locking ring.

FIGS. 7 and 8 show a another embodiment of the locking mechanism of the locking ring. A locking ring 83 is open along a radial cut, and on both sides of the cut two rocker arms 84 and 85 are hingedly secured. By hinges 89, provided as thin material bridges, the rocker arms 84 and 85 are mutually connected as well as connected to the locking ring 83 on respective sides of the radial cut. The locking ring 83 is in FIG. 7 shown in an open position allowing change of ostomy bag, and in FIG. 8 in a locked position in which a not shown ostomy bag can be retained in position relative to a not shown patient part. The rocker arm 85 has a hook 86 which engages with a hook 87 on the locking ring 83.

The locking mechanism is released from the locked position shown in FIG. 8 by touching a tap 88 with a finger so that the hooks 86 and 87 disengage. The hooks 86 and 87 may be so formed that the tap 88 must be activated either radially or axially in order to release the hooks 86 and 87 from their mutual engagement.

The locking ring according to the invention may be made of ordinary plastic materials, e.g. polyethylene or EVA-materials. To ensure that the locking ring is flexible, but not stretchable, it may e.g. be made of a plastic material having a somewhat higher E-modulus, e.g. polypropylene or ABS, or be provided with a fibre reinforcement of such materials.

I claim:

1. A locking ring (3) for an ostomy coupling comprising a first part (1),
   a second part (2) adapted to be coupled in tight-fitting relationship with the first part,
   said first part (1) being intended to be attached to a patient, said second part (2) being intended to be secured to a collection bag, and the locking ring (3) being adapted for mutually retaining said parts,
   characterized in that the locking ring (3) comprises a first locking mechanism (20, 22; 25, 33) with two positions of the locking ring, in which the said first and second parts (1, 2) are mutually loosely connected and mutually locked, respectively, and that the locking ring (3) comprises a second locking mechanism (20, 21, 26, 27) being independent of the first locking mechanism and adapted for retaining and releasing, respectively, the locking ring relatively to one of the said first and second parts.

2. A locking ring according to claim 1, characterized in that the locking mechanisms are released by activation in mutually independent directions.

3. A locking ring according to claim 1, characterized by the locking mechanisms being released by axial and radial activation, respectively.

4. A locking ring according to claim 1, characterized in that it has radially resilient tongues (8) for cooperation with the first part (1).

5. A locking ring according to claim 2, characterized by the locking mechanisms being released by axial and radial activation, respectively.

6. A locking ring according to claim 2, characterized in that it has radially resilient tongues for cooperation with the patient part.

7. A locking ring according to claim 3, characterized in that it has radially resilient tongues for cooperation with the patient part.

* * * * *